(12) United States Patent
Ayers et al.

(10) Patent No.: US 10,827,972 B1
(45) Date of Patent: Nov. 10, 2020

(54) SLEEP STAGING USING AN IN-EAR PHOTOPLETHYSMOGRAPHY (PPG)

(71) Applicant: BOSE CORPORATION, Framingham, MA (US)

(72) Inventors: Tegan M. Ayers, Waltham, MA (US); Christopher R. Paetsch, Cambridge, MA (US); Christian A. Trott, Charleston, SC (US); Brian J. Hetherman, Westborough, MA (US); Matthew Ryan Hicks, Marlborough, MA (US)

(73) Assignee: BOSE CORPORATION, Framingham, MA (US)

( * ) Notice: Subject to any disclaimer, the term of this patent is extended or adjusted under 35 U.S.C. 154(b) by 0 days.

(21) Appl. No.: 16/445,464

(22) Filed: Jun. 19, 2019

(51) Int. Cl.
| | |
|---|---|
| *G08B 23/00* | (2006.01) |
| *A61B 5/00* | (2006.01) |
| *A61B 5/0476* | (2006.01) |
| *A61B 5/08* | (2006.01) |
| *A61B 5/0496* | (2006.01) |
| *A61B 5/04* | (2006.01) |
| *A61B 5/024* | (2006.01) |

(52) U.S. Cl.
CPC .......... *A61B 5/4812* (2013.01); *A61B 5/0059* (2013.01); *A61B 5/0476* (2013.01); *A61B 5/0826* (2013.01); *A61B 5/4818* (2013.01); *A61B 5/6815* (2013.01); *A61B 5/02416* (2013.01); *A61B 5/04012* (2013.01); *A61B 5/0496* (2013.01); *A61B 5/0816* (2013.01); *A61B 5/4809* (2013.01); *A61B 5/4815* (2013.01)

(58) Field of Classification Search
CPC .................................................. A61B 5/4812
USPC ..................................................... 340/575, 576
See application file for complete search history.

(56) References Cited

U.S. PATENT DOCUMENTS

| | | | |
|---|---|---|---|
| 2010/0152560 A1 | 6/2010 | Turcott | |
| 2016/0007934 A1* | 1/2016 | Arnold | A61B 5/1123 600/595 |
| 2016/0029898 A1* | 2/2016 | LeBoeuf | A61B 5/0205 600/301 |

(Continued)

FOREIGN PATENT DOCUMENTS

| | | |
|---|---|---|
| EP | 3377963 A1 | 9/2018 |
| EP | 3378380 A1 | 9/2018 |

OTHER PUBLICATIONS

International Search Report and Written Opinion for International Application No. PCT/US2020/038309 dated Sep. 10, 2020.

(Continued)

*Primary Examiner* — Tai T Nguyen
(74) *Attorney, Agent, or Firm* — Patterson + Sheridan, LLP (57) ABSTRACT

Aspects of the present disclosure provide methods and apparatuses for determining a subject's sleep stage based on a PPG signal measured using an in-ear earpiece. In aspects, one or more physiological signals are estimated based on the PPG. Based, at least in part, on the determined sleep stage, one or more outputs are provided. In an example, the outputs are provided to the subject, the subject's physician, the subject's clinician, the cloud, and/or a device external to the apparatus. The methods and apparatus of determining the subject's sleep state described herein are continuous and non-invasive and eliminate the need for a clinical setting.

21 Claims, 5 Drawing Sheets

(56) References Cited

U.S. PATENT DOCUMENTS

2017/0014035 A1* 1/2017 Newberry .......... A61B 5/02055
2017/0112447 A1* 4/2017 Aumer .................. A61B 5/721
2017/0258329 A1* 9/2017 Marsh ................... G01J 5/0215

OTHER PUBLICATIONS

Thomas Vollmer et al: "Individualized Biomonitoring in Heart Failure—Biomon-HF—"Keep an Eye on Heart Failure—Especially at Night, Biomed Tech 2014; vol. 59, No. 2, Jan. 1, 2014.

* cited by examiner

SLEEP STAGING USING AN IN-EAR PHOTOPLETHYSMOGRAPHY (PPG)

FIELD

Aspects of the present disclosure relate to continuous and accurate determination of a subject's sleep stage based, at least in part, on a photoplethysmogram (PPG) of a subject determined using a PPG sensor positioned on an in-ear audio device. As described herein, one or more outputs are determined based on the sleep stage.

BACKGROUND

Sleep disturbances influence human health. A sleep study or sleep evaluation includes a number of tests performed at the same time while a subject is sleeping. The tests measure specific sleep characteristics to gain a better understanding of the subject's sleep and help to diagnose sleep disorders. Typically, the tests are performed in a sleep lab setting.

Polysomnography (PSG) is the gold standard for sleep evaluation. PSG measures the electrical activity of a subject's brain (electroencephalography, (EEG)), using an electrode cap. PSG also monitors electrooculogram (EOG), electrocardiogram (ECG, EKG), airflow respiratory effort, pulse oximetry, leg or arm EMG, and other biosignals. Once data is collected, a sleep technician scores individual 30-second epochs of the data to determine a corresponding sleep stage and values for one or more other biometric parameters. The scored data, viewed in combination with the subject's medical history, is used to diagnose, or rule out, types of sleep disorders. While PSG and other sleep study methods are informative, there is a need for non-invasively and continuously determining a subject's sleep stage. Ideally, sleep may be monitored in the comfort of the subject's home using minimal equipment.

SUMMARY

All examples and features mentioned herein can be combined in any technically possible manner.

According to aspects, an in-ear audio device is configured to determine, estimate, or calculate a subject's PPG using at least one sensor disposed on the audio device. The subject's sleep stage is determined based on the PPG. In aspects, one or more other physiological signals are measured, estimated, or calculated using the PPG signal. In an example, the sleep stage and other outputs associated with the subject's sleep are provided to the subject, the subject's physician, and/or the subject's clinician. In an example, the sleep stage is used by the in-ear audio device to change the behavior of the audio device based on the determined sleep stage.

Aspects provide a system comprising a PPG sensor disposed on an in-ear earpiece, the PPG sensor configured to measure signals from an ear of a subject wearing the in-ear earpiece and instructions, stored in a memory, that cause at least one processor to: determine a sleep stage of the subject based, at least in part, on the signals and provide an output based on the determined sleep stage.

In an aspect, the instructions cause at least one processor to determine the sleep stage by: transmitting, by a transceiver of the in-ear earpiece, the measured signals to a processor external to the in-ear earpiece and receiving, by the transceiver of the in-ear earpiece, the determined sleep stage from the processor external to the in-ear earpiece.

In an aspect, the processor external to the in-ear earpiece has instructions stored in a memory that cause the processor external to the in-ear earpiece to estimate one or more physiological signals based on the measured signals, and determine the sleep stage of the subject based, at least in part, the one or more physiological signals.

In an aspect, the one or more physiological signals comprise one of: heart rate (HR), heart rate variability (HRV), respiration rate (RR), respiration rate variability (RRV) or blood oxygenation level.

In an aspect, the processor external to the in-ear earpiece has instructions stored in the memory that further cause the processor external to the in-ear earpiece to: transmit the determined sleep stage to the in-ear earpiece.

In an aspect, the instructions cause the processor external to the in-ear earpiece to determine the sleep stage of the subject by: estimating the sleep stage using a machine learning algorithm. In an aspect, the instructions cause the processor external to the in-ear earpiece to estimate one or more physiological signals by: estimating the one or more physiological signals using a machine learning algorithm.

In an aspect, the instructions cause the at least one processor to provide the output based on the determined sleep stage by: outputting, via an application running on a wireless device in communication with the in-ear earpiece, a hypnogram illustrating the determined sleep stage as a function of time for a given sleep period.

In an aspect, the sleep stage comprises one of: wake, N1, N2, N3, and rapid eye movement (REM) sleep stages.

In an aspect, the signals are measured from one of the concha, the ear canal, or a region between the concha and the ear canal of the subject.

Aspects provide a method for determining a sleep stage of a subject comprising: measuring signals collected using a PPG sensor disposed on an in-ear earpiece, determining the sleep stage of the subject based, at least in part, on the measured signals, and providing an output based on the determined sleep stage.

In an aspect, determining the sleep stage comprises: transmitting, by an in-ear ear piece, the measured signals to a processor external to the in-ear earpiece and receiving, by the in-ear earpiece, the determined sleep stage from the processor.

In an aspect, the method further comprises estimating, by the processor, one or more physiological signals based on the measured signals and determining, by the processor, the sleep stage of the subject based, at least in part, the one or more physiological signals.

In an aspect, the one or more physiological signals comprise one of: heart rate (HR), heart rate variability (HRV), respiration rate (RR), respiration rate variability (RRV) or blood oxygenation level.

In an aspect, the method further comprises transmitting, by the processor, the determined sleep stage to the in-ear earpiece. In an aspect, determining the sleep stage of the subject comprises estimating the sleep stage using a machine learning algorithm. In an aspect, estimating the one or more physiological signals comprises estimating the one or more physiological signals using a machine learning algorithm.

In an aspect, wherein providing the output based on the determined sleep stage comprises outputting, via an application running on a wireless device in communication with the in-ear earpiece, a hypnogram illustrating the determined sleep stage as a function of time for a given sleep period.

Aspects provide an in-ear earpiece comprising: a PPG sensor configured to measure signals from a subject wearing the earpiece and instructions, stored in a memory, that cause at least one processor to: determine a sleep stage of the subject based, at least in part, on the signals and provide an output based on the determined sleep stage to the subject. In an aspect, the sleep stage is determined based on one or more physiological signals estimated using the measured signals.

Two or more features described in this disclosure, including those described in this summary section, can be combined to form implementations not specifically described herein. The details of one or more aspects are set forth in the accompanying drawings and the description below. Other features, objects, and advantages will be apparent from the description, drawings, and the claims.

DETAILED DESCRIPTION

PPG sensors optically detect changes in the blood flow volume (i.e., changes in the detected light intensity) in the microvascular bed of tissue. PPG is detected via reflection from or transmission through the tissue. PPG sensors can be used to estimate a variety of biometric parameters. Fingertip and earlobe measures are currently used; however, these locations may have limited blood perfusion. In addition, conventional fingertip or earlobe PPG sensors may not be ideal for taking measurements over a long period of time, such as during a sleep period.

Figure 1:
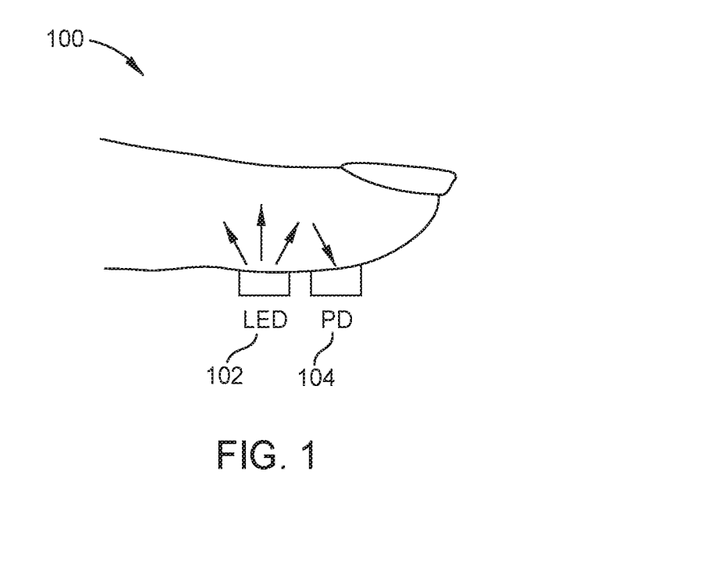
FIG. 1 illustrates an example technique for using a fingertip sensor to determine a PPG.

FIG. 1 illustrates an example technique 100 for using a fingertip sensor to determine a PPG. A PPG sensor measures changes in blood volume within a blood vessel using a light emitting diode (LED) 102 and photodetector (PD) 104. In an example, the LED 102 emits a light of a known wavelength, such as 640 nm (red) or 910 nm (infrared) through the soft tissue. The PD 104 detects light that is back-scattered or reflected from one or more of the tissue, bone, and/or blood vessels. The modulation of reflected light correlates to the volume of blood in the arteries. The modulation of reflected light creates a pulsatile waveform indicative of the heart beating.

A PPG can be used to detect a variety of biometric parameters, including, but not limited to, heart rate as described with reference to FIG. 2, respiration rate (RR) as described with reference to FIG. 3, heart rate variability (HRV), respiration rate variability (RRV), peripheral capillary oxygen saturation (SpO2) level, blood pressure, cholesterol, heart disease, blood glucose, stress, and hemoglobin A1C level.

Figure 2:
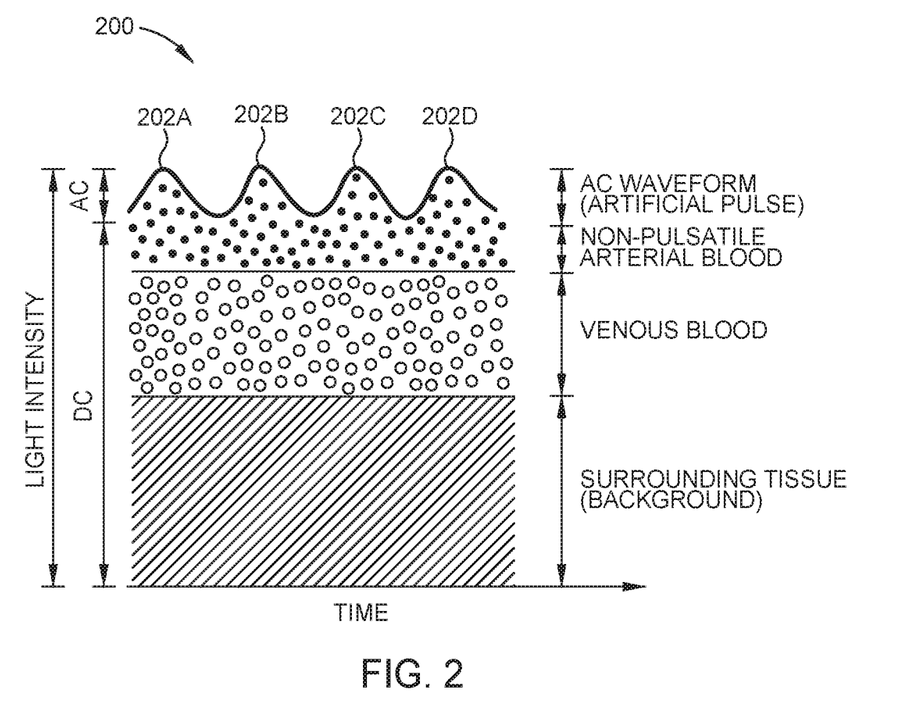
FIG. 2 illustrates an example PPG waveform.

FIG. 2 illustrates an example PPG waveform 200. Peaks 202A-202D in the waveform 200 correspond to heart beats. Accordingly, a PPG signal is used to determine or monitor the subject's heart beats.

Figure 3:
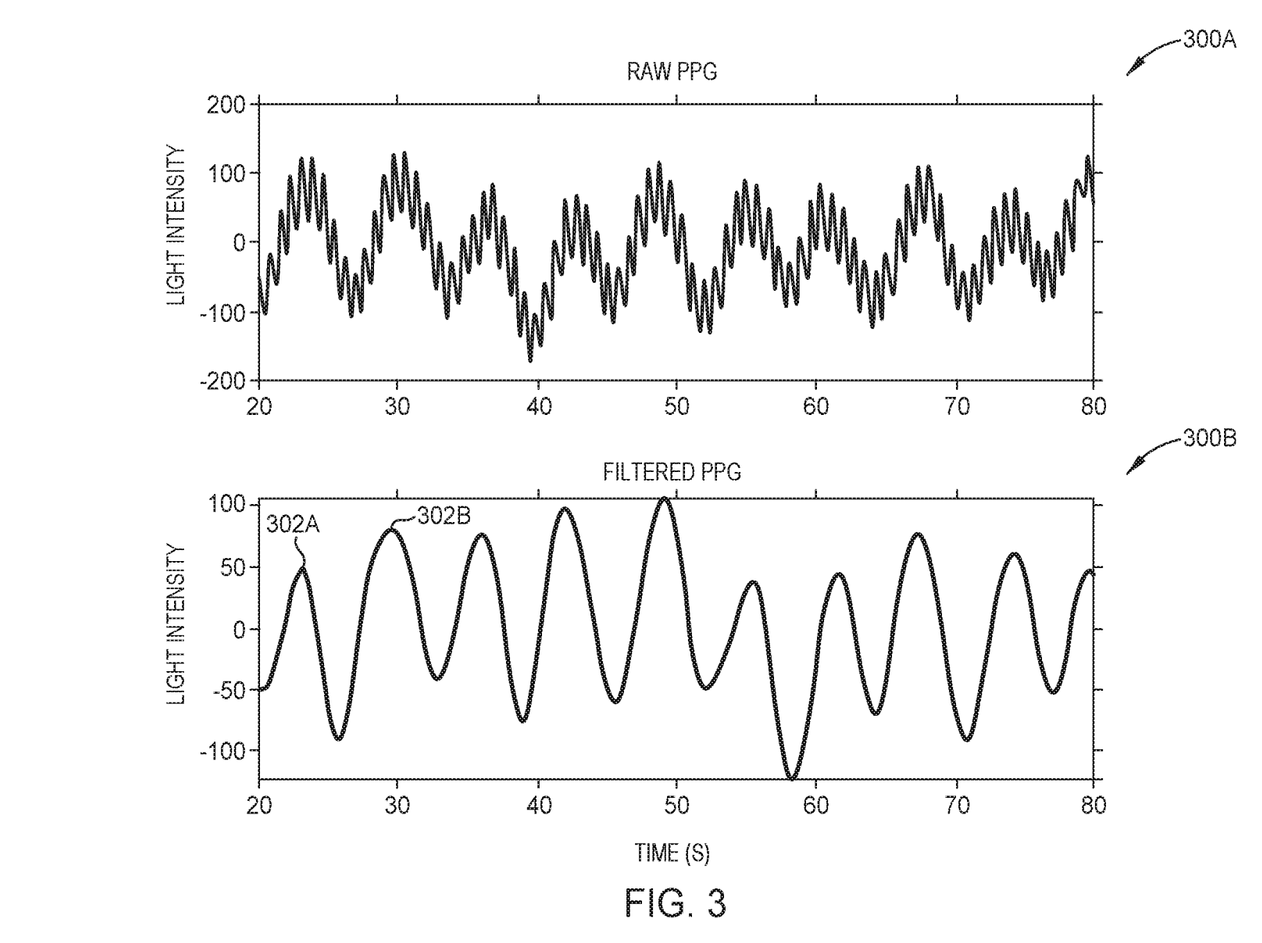
FIG. 3 illustrates raw and bandpass filtered PPG waveforms correlating to a respiration waveform.

FIG. 3 illustrates a raw PPG waveform 300A and a filtered PPG waveform 300B used to determine a subject's RR. RR is included as low frequency content (e.g., 0.1-0.4 Hz) within the PPG signal. To extract a subject's RR, a raw PPG signal 300A is bandpass filtered, and the power spectral content is identified, for example, through performing a Fourier Transform on the signal. Peaks, such as peaks 302A and 302B in the resulting filtered PPG signal 300B, indicate the subject's RR. The subject's HRV can be determined from the time between peaks in the signal.

Typically, a subject passes through five stages of sleep: wake, N1, N2, N3, and rapid eye movement (REM) sleep. The order of each stage and amount of time spent in each stage may differ across subjects. In an example, a subject repeatedly transitions from wake, N1, N2, N3, N2, perhaps N1, REM, and perhaps N1 in a sleep cycle. A sleep cycle may last approximately 90 minutes. In subsequent sleep cycles of a sleep period, the subject may spend less time in N3. In the last few sleep cycles of a sleep period, the subject may spend an increased amount of time in N1. In another example, a subject transitions form wake, to N1, N2, N3, and REM. In yet another example, a subject wakes for a brief period of time and returns to the previous sleep stage or a sleep stage one off from the previous sleep stage.

N1 may be called sleep transition because a subject transitions from being awake to being asleep. N2 may be referred to as light sleep. N2 is the stage of sleep subjects are in for the majority of the night. N3 may be referred to a deep sleep. N3 is the stage of sleep most related to body restoration and metabolic function. REM sleep tends to be restorative to the mind and related to memory consolidation.

Research has shown that a sleep stage can be determined using various physiological biosignals, such as HR, HRV, RR, and RRV. For example, HRV is highest when awake, due to sympathetic nervous system dominance and the HRV is lowest during deep sleep due to parasympathetic nervous system dominance.

Figure 4:
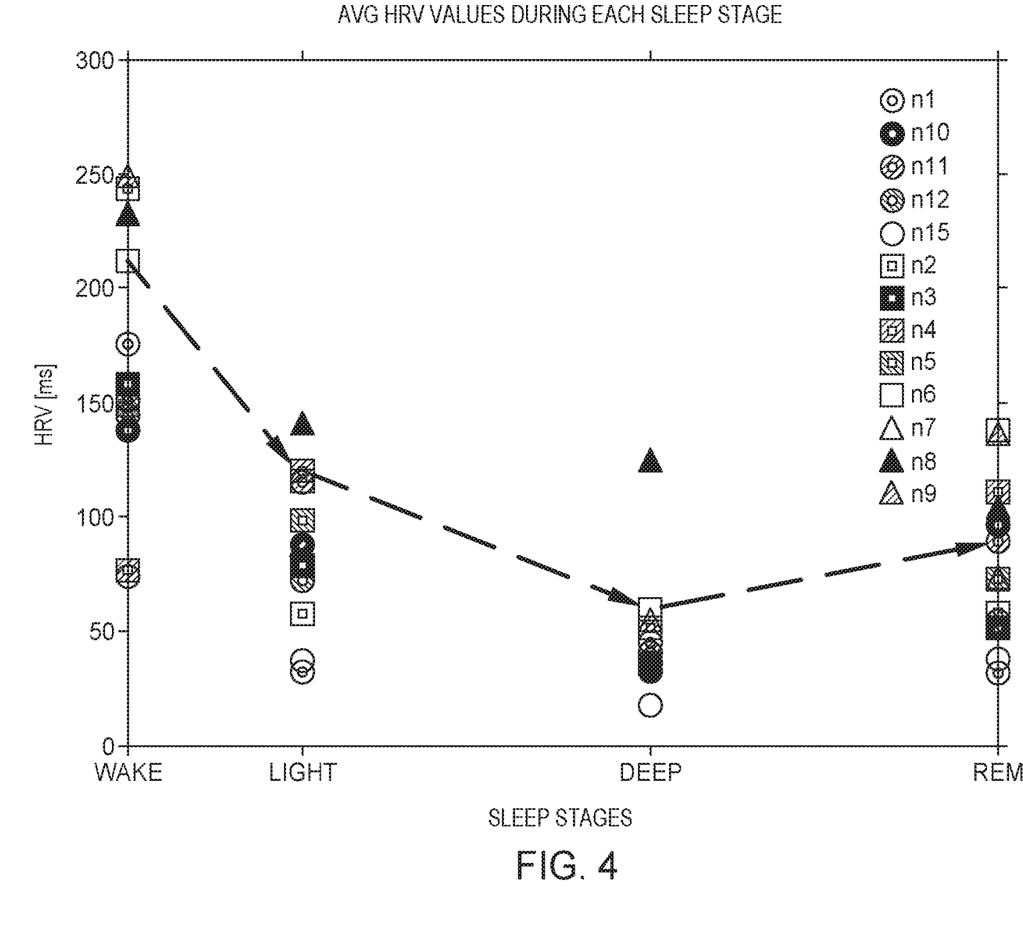
FIG. 4 illustrates heart rate variability (HRV) as a function of sleep stage.

FIG. 4 illustrates average HRV values during each sleep stage. At 400, FIG. 4 illustrates an average HRV for 13 subjects. Each arrow tracks a single subject's HRV as a function of sleep stage. The dashed line 404 shows the HRV for subject 402 through the sleep stages of one sleep cycle. When awake, the subject's HRV was just greater than 200. The HRV for the subject in light sleep (N2) was approximately 125, the HRV for the subject during deep sleep (N3) was approximately 75, and the HRV for the subject during REM was approximately 90.

Figure 5:
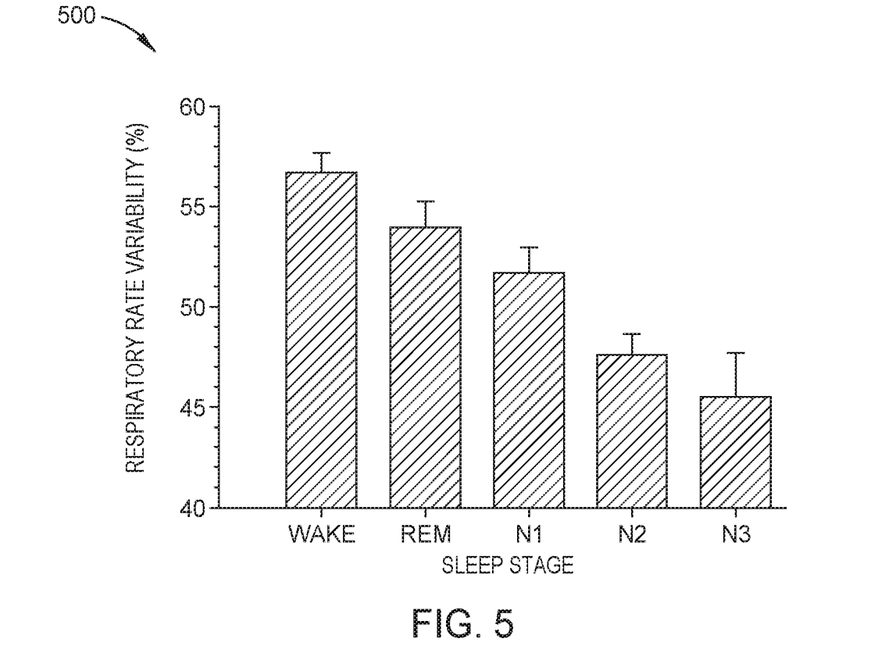
FIG. 5 illustrates respiration rate variability (RRV) as a function of sleep stage.

Similar to HRV, other biometrics trend as a function of sleep stage. HR and RR can both be used to determine between awake versus asleep (rather than specific sleep stages). Each of HR and RR tend to decrease as a subject drifts from awake to asleep. Respiration rate variability (RRV), similar to HRV, shows more definitive trends in relation to sleep stages. At 500, FIG. 5 illustrates that RRV is greatest during wake and REM and decreases during N1, N2, and N3.

Various biometrics, including those described above, can be estimated or determined using a PPG sensor. Further, the estimated or determined biometrics indicate a sleep stage and provide useful information about the subject's sleep. In view of the shortcomings of traditional sleep studies, aspects provide methods and apparatus for a non-invasive, continuous, and accurate determination of a subject's sleep stage. Specifically, aspects provide a PPG sensor configured to measure signals from an ear of a subject wearing an in-ear earpiece. At least one processor, either internal or external to the in-ear earpiece, has instructions stored in memory that are configured to cause the at least one processor to (1) determine a sleep stage of the subject based, at least in part, on the PPG signals and (2) provide one or more outputs. In an example, the outputs are provided to a user, user's clinician, or user's physician based on the determined sleep stage. In an aspect, the outputs are stored internal or external to the in-ear earpiece, displayed internal or external to the in-ear earpiece, or used externally to the in-ear earpiece. Additionally or alternatively, the sleep stage is used to change the behavior of the in-ear audio earpiece based on the determined sleep stage. For example, the in-ear earpiece may change an audio output based on the determined sleep stage in an effort to protect sleep.

Aspects describe N1, N2, N3, and REM as sleep stages for illustrative purposes; however, the phrase "sleep stage" is not so limited. In an aspect, the determined sleep stages include wake, light sleep (N1 or N2), deep sleep (N3), and REM. In yet other aspects, sleep stages include wake, non-REM (N1, N2, or N3), and REM. In other aspects, sleep stages include wake and sleep (N1, N2, N3, or REM).

Figure 6:
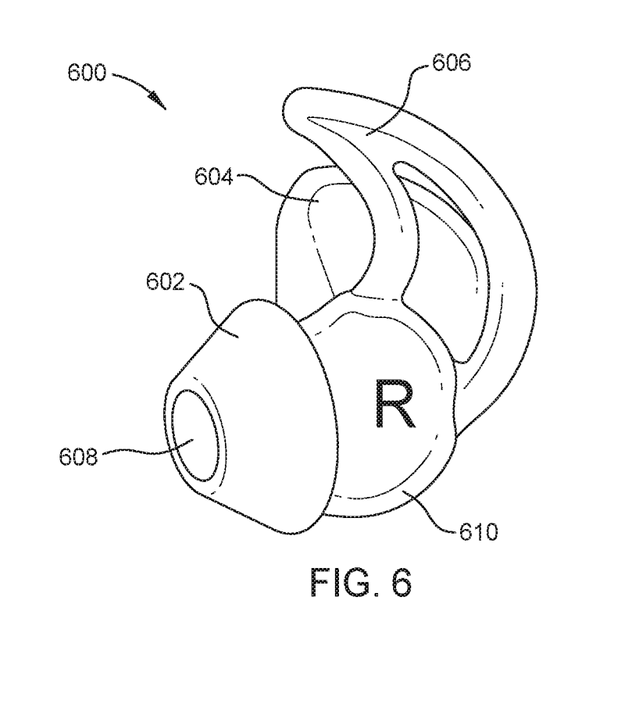
FIG. 6 illustrates an example in-ear earpiece.

FIG. 6 illustrates an example of an in-ear earpiece. 600. The earpiece 600 includes an earbud 604 that houses an acoustic driver module and is coupled to a body 610, a nozzle 608 extending from a body 610 of the earpiece towards a substantially frusto-conical sealing structure 602 (called an ear tip), and a positioning and retaining structure 606.

The 610 of the earpiece 600 is substantially elliptical or circular in shape to align with typical ear geometries. In an example, the body 610 is coupled to the earbud 604. In aspects, the earbud 604 includes an acoustic driver module. In an example, the earbud 604 includes electronic modules (not shown) for wirelessly communicating with external devices and networks.

A nozzle 608 extends from the body 610 towards the ear canal of the subject's ear. The nozzle includes an acoustic passage to conduct sound waves to the ear canal of the subject.

The in-ear earpiece provides enough surface area to contact the subject's skin when positioned in-ear. The soft, flexible material of the ear tip sealing structure 602 helps the tip to conform to the subject's ear geometry and increases the surface area having contact with a subject's skin. Additionally, the flare of the umbrella-shaped ear tip 602 provides some springiness so that some pressure is exerted by the ear tip 602 on the subject's skin.

The positioning and retaining structure 606 holds the earpiece in position in a subject's ear, without significant contribution from the portions of the ear tip that engage the ear canal and without any structure external to the ear tip. In an example, as shown in FIG. 6, the earpiece 600 includes a positioning and retaining structure 606 having an outer leg and an inner leg; however, the disclosure is not limited to an ear tip having two legs. In an example, an ear tip includes a single leg extending from the body and configured to follow the curve of the anti-helix and/or the cymba concha at the rear of the concha.

In aspects, the earpiece 600 is connected, either via a wired connection or a wireless connection, to a second earpiece configured to fit in subject's right ear. In aspects, the earpiece is part of a wearable form factor, such as audio eyeglasses, headsets, or a sleep mask.

The in-ear earpiece includes at least one PPG sensor. In one aspect, the sensor includes an LED and a PD as shown in FIG. 1. In an example, the PPG sensor is disposed on the earbud 604, in a region that contacts the body 610 of the earpiece 600. In an example, the LED and PD are housed on or inside the nozzle 608 of the earbud. When the sensor is contained within the nozzle, the light from the LED effectively passes through the tip 602 with little or no interference from the tip. In another example, the LED and PD are disposed on the back side of the umbrella tip, so that the light from the LED shines through the ear tip 602 and into the subject's ear canal. The PD measures the light that is reflected back. In another aspect, the ear tip includes multiple emitters and collectors. In an aspect, at least some of the multiple emitters and collectors are positioned on the back side of the umbrella tip. In an example, at least some of the collectors and emitters form a circular or semi-circular shape. In aspects, the PPG sensor contacts the subject's concha or the subject's ear canal. In an aspect, the PPG sensor contacts a region between concha and the ear canal of the subject.

Generally, the PPG sensor is disposed anywhere on the earpiece 600 where the PPG sensor is able to collect an in-ear PPG signal.

In addition to the PPG sensor, in aspects, the earpiece 600 includes one or more of a memory and processor, communication unit, transceiver, and audio output transducer or speaker. In an aspect, any of the PPG sensor, memory and processor, communication unit, transceiver, and audio output transducer are configured to communicate with each other. In an example, all of these components are coupled to and communicate with each other.

The memory and processor control the operations of the earpiece 600. The memory stores program code for controlling the memory and processor. The memory may include Read Only Memory (ROM), a Random Access Memory (RAM), and/or a flash ROM. The processor controls the general operation of the earpiece 600. The processor performs process and control for audio and/or data communication. In some aspects, in addition to the general operation, the processor is configured to determine a subject's PPG, determine a sleep stage, and determine one more outputs based on the determined sleep stage. In aspects, the processor is configured to output the determined PPG, sleep stage, and/or outputs determined based on the sleep stage. In an example, the processor, in combination with one or more other components of the earpiece, perform the operations described herein.

The communication unit facilitates a wireless connection with one or more other devices. For example, the communication unit may include one or more wireless protocol engines such as a Bluetooth engine. While Bluetooth is used as an example protocol, other communication protocols may also be used. Some examples include Bluetooth Low Energy (BLE), Near Field Communications (NFC), IEEE 802.11, or other local area network (LAN) or personal area network (PAN) protocols.

In an example, the communication unit wirelessly communicates with an external device, such as a bedside unit, a tablet, a cell phone, a smart device, or the cloud. By communicating with the cloud, devices in communication with the cloud which may or may not be in direct communication with the earpiece 600 may access the sleep information.

In an example, the communication unit wirelessly communicates an indication of the collected PPG waveform. External devices or cloud may determine the subject's PPG from the waveform, the subject's sleep stage, and one or more outputs based, at least in part, on the subject's sleep stage. Further, determined sleep stages may be stored on the cloud, and displayed via a web site or applications is in direct or indirect communication with the in-ear earpiece.

In an aspects, the earpiece communicates with an external device through a wired connection. The external device receives an indication of the collected PPG waveform from the earpiece through the wired connection, determines the subject's PPG from the waveform, the subject's sleep stage, and one or more other outputs based, at least in part, on the subject's sleep stage. The external device transmits the sleep stage and other outputs to the earpiece through the wired connection or the external device wirelessly transmits the sleep stage and other outputs to yet another device or network.

The transceiver transmits and receives information via one or more antennae to exchange information with one or more other devices and/or the cloud. The transceiver is not necessarily a distinct component. The audio output transducer may be also known as a driver or speaker. In some examples, more than one output transducer is used. The transducer converts electrical signals into sound and converts sound into electrical signals. In aspects, the transducer adjusts an audio output by the earpiece 600 based on a determined sleep stage.

The earpiece 600 is provided for illustrative purposes only. Aspects of the disclosure are not limited to the specific form factor illustrated in FIG. 6 or described with reference to FIG. 6. According to aspects, any in-ear earpiece including a PPG sensor is used to determine a subject's sleep stage based on the collected PPG and configured to provide any number of outputs related to the subject's sleep to the subject or other people.

As described above, the in-ear PPG sensor collects a signal used to determine the subject's PPG. In an example, a processor onboard the in-ear earpiece determines the sleep stage based on the collected PPG signal.

In another example, a transceiver in the in-ear earpiece transmits the measured PPG signal to an external processor, network, or cloud server. The external processor, network, or cloud server processes the PPG signal to determine the subject's sleep stage. The determined sleep stage is transmitted by the processor, network, or cloud server to the in-ear earpiece or directly to an external device such as any smart device.

Regardless of where the PPG signal is processed, one or both of the in-ear earpiece and processor external to the in-ear earpiece are also configured to determine any number of physiological signals based, at least in part, on the obtained PPG signal. Non-limiting examples of physiological signals include HR, HRV, RR, RRV, and blood oxygenation level. The sleep stage can be determined based on the PPG signal or the PPG signal and any combination of the estimated physiological signals.

In one example, the in-ear earpiece estimates physiological signals from the collected PPG to determine a sleep stage of the subject. The determined sleep stage is transmitted by the in-ear earpiece to another device for output. In aspects, the information regarding estimated physiological signals is also transmitted by the in-ear earpiece to another device for output. In another example, a processor external to the in-ear earpiece estimates one or more physiological signals from the collected PPG, determines a sleep stage of the subject, and transmits the determined sleep stage to the in-ear earpiece or another device for output.

Two overarching methods are provided for determining a sleep stage using information obtained from an in-ear PPG sensor. In both methods, a machine learning algorithm is used to determine the sleep stage and provide an output. The person may be the subject wearing the in-ear earpiece, a subject's clinician, and/or the subject's physician.

According to a first technique, physiological signals are extracted from the PPG signal and the extracted physiological signals are input into a machine learning model. Physiological signals are extracted from the PPG signal using low pass filtering, linear smoothing, and other processing techniques. Through supervised learning, the machine learning algorithm learns a relationship between each one of the physiological signal inputs and the output sleep stage.

The machine learning algorithm receives ground truth, for example from clinical PSGs, and data collected from the subject's in-ear PPG sensor. Through supervised learning, the algorithm learns relationships between each of the physiological signals obtained from the PPG signal and between the physiological signals and a sleep stage.

In one example, peaks of a PPG signal are identified and a standard deviation of the time between the peaks results in an estimate of the subject's HRV. HRV is input into the machine learning algorithm. Other features, such as HR and RR, may be also be extracted from the PPG signal and input into the algorithm. The machine learning algorithm compares the input features with known relationships to determine a subject's sleep stage at a particular time.

According to a second technique, the raw PPG signal is input into a machine learning algorithm. In an example, the PPG signal, without pre-processing, is input into a neural network. The neural network determines the features, relationships between the features, and relationships between one or more of the features and a sleep stage. Examples of features include any physiological signal or characteristic of the raw PPG waveform, such as amplitude or period of the signal. Inputting the raw PPG signal into the model may be computationally intensive relative to inputting features into a machine learning algorithm; however, this technique provides increased flexibility because the model may find new features and associations between features and between features and a sleep stage.

Figure 7:
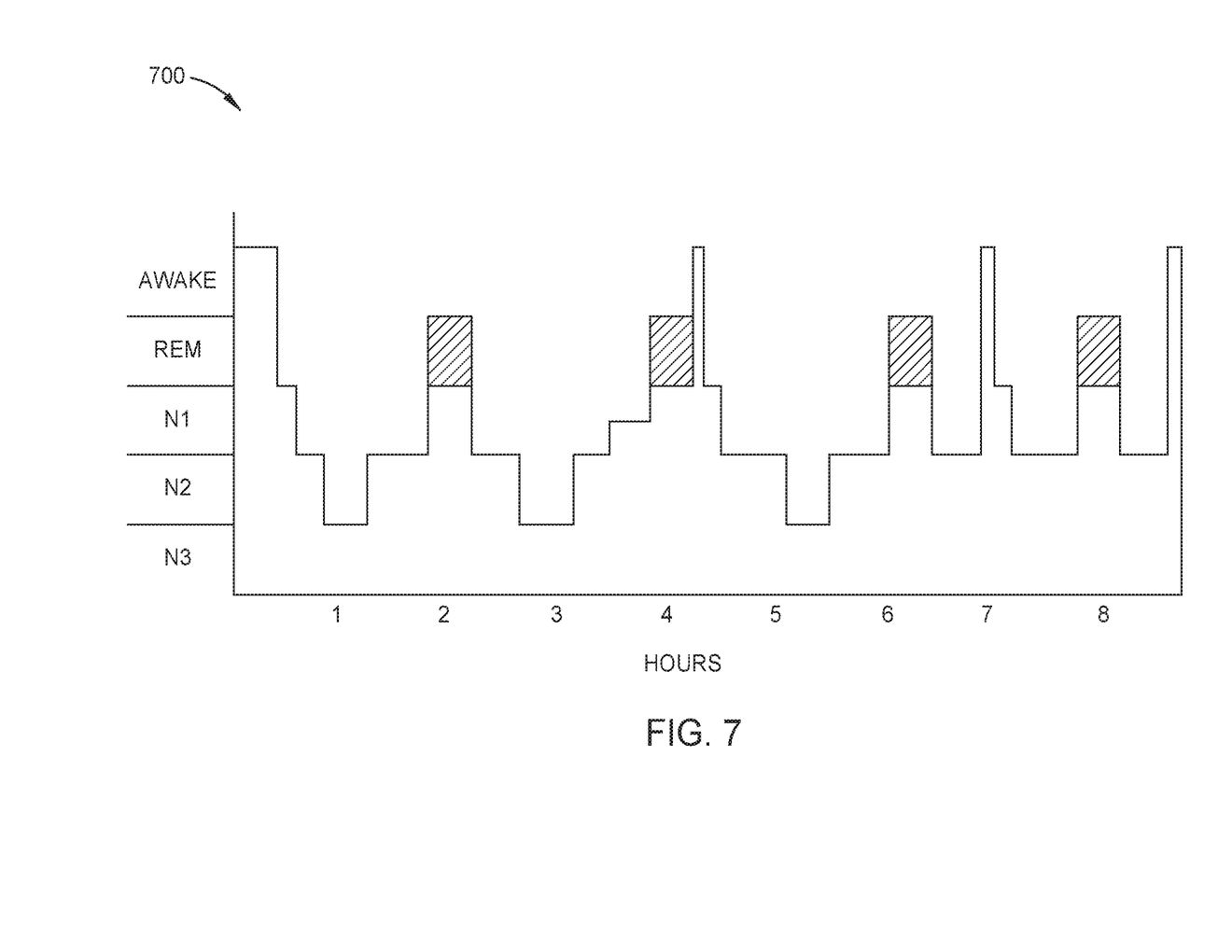
FIG. 7 illustrates an example output determined based, at least in part, on the PPG signal collected using a PPG sensor disposed on an in-ear earpiece.

FIG. 7 illustrates an example of an output 700 generated based on a subject's determined sleep stage. The output 700 is displayed on a device in communication with the in-ear earpiece. In one example, the output is displayed on an application running on the subject's cell phone or tablet. The hypnogram displayed in FIG. 7 represents the stages of sleep as a function of time. People may easily understand the amount of time slept in each sleep stage, and therefore how the subject slept in a sleep period, through the visual representation shown in FIG. 7. In aspects, the hypnogram displays arousal events (brief period of wake) followed by returning to the previous sleep stage, or returning to a sleep stage one off from the previous sleep stage.

In addition to outputting a sleep stage, outputs provided to the subject, a clinician, and/or a physician include one or more sleep statistics, suggested behavioral changes, medical diagnosis, and intelligent audio output adjustments based on the sleep stage. In aspects, the output based on the determined sleep stage includes a sleep latency indicating how long it took the user to fall asleep, how long the user slept in a given sleep period, the number of times the user woke up in a given period of time, and/or a sleep score that summarizes the quality of the user's sleep over a sleep period. In an example, the sleep score includes any combination of outputs described herein. Any combination of these outputs are displayed on an application running on the subject's cell phone or tablet.

Sleep statistics include information such as how long it took a subject to fall asleep, the time the subject fell asleep, and the time the subject woke up in one sleep period. In an aspect, a sleep score that indicates the subject's overall sleep quality is output.

According to aspects, suggested behavioral changes include a virtual sleep coach running on an application in communication with the in-ear earpiece suggesting behavioral modifications based on the subject's prior monitored sleep. In an example, the sleep coach suggests that the subject go to sleep earlier based on how the subject slept the night before. In another example, the sleep coach encourages the subject to decrease caffeine or alcohol consumption based on how the subject slept the night before.

According to aspects, the output provides an indication encouraging the subject to seek medical attention because of unhealthy sleeping patterns, abnormal sleeping, or based on observed symptoms associated with a medical condition such as insomnia or sleep apnea.

According to aspects, based on the determined sleep stage, the in-ear earpiece intelligently transitions between different stimuli. Initially, a first stimulus is output by the in-ear earpiece to help guide the subject to fall asleep. When the subject is determined to be asleep, the in-ear earpiece transitions from outputting the first stimulus to outputting a second stimulus that protects the subject's sleep. In another example, the in-ear earpiece adjusts a level of noise masking when the subject is determined to be asleep.

Aspects describe an in-ear earpiece including a PPG sensor configured to measure signals from a wearer, determine a sleep stage of the subject based on the PPG, and provide an output based on the determined sleep stage. The methods for monitoring the subject's sleep described herein eliminate the need for a sleep lab setting and clinician scoring the subject's sleep. Due to the form factor, a subject's sleep is continuously monitored in a non-invasive manner. Using a machine learning algorithm to determine a sleep stage and other outputs provides consistent sleep scoring across multiple people and multiple sleep sessions.

In the preceding, reference is made to aspects presented in this disclosure. However, the scope of the present disclosure is not limited to specific described aspects. Aspects of the present disclosure may take the form of an entirely hardware embodiment, an entirely software embodiment (including firmware, resident software, micro-code, etc.) or an embodiment combining software and hardware aspects that may all generally be referred to herein as a "component," "circuit," "module" or "system." Furthermore, aspects of the present disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples of a computer readable storage medium include: an electrical connection having one or more wires, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the current context, a computer readable storage medium may be any tangible medium that can contain or store a program.

The flowchart and block diagrams in the Figures illustrate the architecture, functionality and operation of possible implementations of systems, methods and computer program products according to various aspects. In this regard, each block in the flowchart or block diagrams may represent a module, segment or portion of code, which comprises one or more executable instructions for implementing the specified logical function(s). In some implementations, the functions noted in the block may occur out of the order noted in the figures. For example, two blocks shown in succession may, in fact, be executed substantially concurrently, or the blocks may sometimes be executed in the reverse order, depending upon the functionality involved. Each block of the block diagrams and/or flowchart illustrations, and combinations of blocks in the block diagrams and/or flowchart illustrations can be implemented by special-purpose hardware-based systems that perform the specified functions or acts, or combinations of special purpose hardware and computer instructions.

The invention claimed is:

1. A system comprising:
a photoplethysmogram (PPG) sensor disposed on an in-ear earpiece, the PPG sensor configured to measure light signals from an ear of a subject wearing the in-ear earpiece, wherein the in-ear earpiece comprises:
a nozzle coupled to a sealing structure, the nozzle extending toward an ear canal of the subject to conduct sound waves to the ear canal of the subject and housing the PPG sensor, and the sealing structure configured to create a seal with an entrance to the ear canal and provide a light source for generating the light signals; and
instructions, stored in a memory, that cause at least one processor to:
determine a sleep stage of the subject based, at least in part, on the light signals; and
provide an output based on the determined sleep stage.

2. The system of claim 1, wherein the instructions cause the at least one processor to determine the sleep stage by:
transmitting, by a transceiver of the in-ear earpiece, the measured light signals to a processor external to the in-ear earpiece; and
receiving, by the transceiver of the in-ear earpiece, the determined sleep stage from the processor external to the in-ear earpiece.

3. The system of claim 2, wherein the processor external to the in-ear earpiece has instructions stored in a memory that cause the processor external to the in-ear earpiece to:
estimate one or more physiological signals based on the measured light signals; and
determine the sleep stage of the subject based, at least in part, the one or more physiological signals.

4. The system of claim 3, wherein the one or more physiological signals comprise one of: heart rate (HR), heart rate variability (HRV), respiration rate (RR), respiration rate variability (RRV) or blood oxygenation level.

5. The system of claim 3, wherein the processor external to the in-ear earpiece has instructions stored in the memory that further cause the processor external to the in-ear earpiece to:
transmit the determined sleep stage to the in-ear earpiece.

6. The system of claim 3, wherein the instructions cause the processor external to the in-ear earpiece to determine the sleep stage of the subject by:
estimating the sleep stage using a machine learning algorithm.

7. The system of claim 3, wherein the instructions cause the processor external to the in-ear earpiece to estimate one or more physiological signals by:
estimating the one or more physiological signals using a machine learning algorithm.

8. The system of claim 1, wherein the instructions cause the at least one processor to provide the output based on the determined sleep stage by:
  outputting, via an application running on a wireless device in communication with the in-ear earpiece, a hypnogram illustrating the determined sleep stage as a function of time for a given sleep period.

9. The system of claim 1, wherein the sleep stage comprises one of: wake, N1, N2, N3, and rapid eye movement (REM) sleep stages.

10. The system of claim 1, wherein the light signals are measured from one of: the ear canal, a concha corresponding to the ear canal, or a region between the concha and the ear canal of the subject.

11. The system of claim 1, wherein the output is provided to a person.

12. A method for determining a sleep stage of a subject comprising:
  measuring light signals collected using a photoplethysmogram (PPG) sensor disposed on an in-ear earpiece, wherein the in-ear earpiece comprises: a nozzle coupled to a sealing structure, the nozzle extending toward an ear canal of the subject to conduct sound waves to the ear canal of the subject and housing the PPG sensor, and the sealing structure configured to create a seal with an entrance to the ear canal and provide a light source for generating the light signals;
  determining the sleep stage of the subject based, at least in part, on the measured light signals; and
  providing an output based on the determined sleep stage.

13. The method of claim 12, wherein determining the sleep stage comprises:
  transmitting, by an in-ear ear piece, the measured light signals to a processor external to the in-ear earpiece; and
  receiving, by the in-ear earpiece, the determined sleep stage from the processor.

14. The method of claim 13, further comprising:
  estimating, by the processor, one or more physiological signals based on the measured light signals; and
  determining, by the processor, the sleep stage of the subject based, at least in part, the one or more physiological signals.

15. The method of claim 14, wherein the one or more physiological signals comprise one of: heart rate (HR), heart rate variability (HRV), respiration rate (RR), respiration rate variability (RRV) or blood oxygenation level.

16. The method of claim 14, further comprising:
  transmitting, by the processor, the determined sleep stage to the in-ear earpiece.

17. The method of claim 14, wherein determining the sleep stage of the subject comprises:
  estimating the sleep stage using a machine learning algorithm.

18. The method of claim 14, wherein the estimating the one or more physiological signals comprises:
  estimating the one or more physiological signals using a machine learning algorithm.

19. The method of claim 12, wherein providing the output based on the determined sleep stage comprises:
  outputting, via an application running on a wireless device in communication with the in-ear earpiece, a hypnogram illustrating the determined sleep stage as a function of time for a given sleep period.

20. An in-ear earpiece comprising:
  a photoplethysmogram (PPG) sensor configured to measure light signals from a subject wearing the in-ear earpiece, wherein the in-ear earpiece comprises: a nozzle coupled to a sealing structure, the nozzle extending toward an ear canal of the subject to conduct sound waves to the ear canal of the subject and housing the PPG sensor, and the sealing structure configured to create a seal with an entrance to the ear canal and provide a light source for generating the light signals; and
  instructions, stored in a memory, that cause at least one processor to:
  determine a sleep stage of the subject based, at least in part, on the light signals; and
  provide an output based on the determined sleep stage to the subject.

21. The in-ear earpiece of claim 20, wherein the sleep stage is determined based on one or more physiological signals estimated using the measured light signals.

* * * * *